United States Patent
Li et al.

(10) Patent No.: US 10,149,807 B1
(45) Date of Patent: Dec. 11, 2018

(54) ALCOHOL-REMOVABLE NAIL GEL AND ITS MANUFACTURING METHOD

(71) Applicant: AnnGel Cosmetics LLC, Cedar Grove, NJ (US)

(72) Inventors: Pingjun Li, Guangdong (CN); Mujuan Jiang, Guangdong (CN); Haidi Xian, Guangdong (CN)

(73) Assignee: GELAB COSMETICS LLC., Cedar Grove, NJ (US)

( * ) Notice: Subject to any disclaimer, the term of this patent is extended or adjusted under 35 U.S.C. 154(b) by 0 days.

(21) Appl. No.: 15/980,072

(22) Filed: May 15, 2018

(30) Foreign Application Priority Data

Aug. 2, 2017 (CN) .......................... 2017 1 0653355

(51) Int. Cl.
*A61K 8/37* (2006.01)
*A61Q 3/02* (2006.01)
*A61K 8/42* (2006.01)
*A61K 8/73* (2006.01)
*A61K 8/55* (2006.01)

(52) U.S. Cl.
CPC ................. *A61K 8/37* (2013.01); *A61K 8/42* (2013.01); *A61K 8/55* (2013.01); *A61K 8/731* (2013.01); *A61Q 3/02* (2013.01); *A61K 2800/43* (2013.01)

(58) Field of Classification Search
None
See application file for complete search history.

(56) References Cited

U.S. PATENT DOCUMENTS 6,673,850 B1 * 1/2004 Yamato ................. C07C 323/54
522/153

* cited by examiner

*Primary Examiner* — Nannette Holloman
(74) *Attorney, Agent, or Firm* — Enshan Hong; VLP Law Group LLP

(57) ABSTRACT

An alcohol-removable nail gel comprising the following components in percent by weight:
isobornyl acrylate 10-15%
hydroxyethyl methacrylate 15-25%
trimethylolpropane triacrylate 5-15%
(2,4,6-trimethylbenzoyl)diphenylphosphine oxide 5-15%
aliphatic urethane acrylate 20-30%
cellulose acetate butyrate 15-20%
pigments 1-15%. The alcohol removable gel polish, similar in application and function as common one-step gel polish, can be removed with alcohol solution which does not contain acetone, ethyl acetate, butyl acetate or other toxic solvents. Using alcohol-soaked cotton to wrap nails for 10-15 min, the process is environmentally friendly, safe, healthy and not detrimental to human body.

8 Claims, No Drawings

ALCOHOL-REMOVABLE NAIL GEL AND ITS MANUFACTURING METHOD

BACKGROUND OF THE INVENTION

1. Field of the Invention

The invention relates to personal care products, more specifically, an alcohol removable nail gel, and preparation of the same.

2. Description of the Related Art

Currently, the nail care products in the market can be mainly categorized into nail lacquer polish and nail gel polish. When nail gel is applied on nails, it can be fully cured by irradiation of ordinary UV or UV-LED light sources within a few minutes. Compared with lacquer polish, the raw materials of gel polish are obtained from UV resin, which is less toxic, low odor, and more environmentally friendly. The color of gel polish is full and clear, easy to apply, quick-dry, and more durable. Hence, it is increasingly popular on the market.

One-step nail gel polish is a three-in-one product (i.e. a combination of base coat, color coat, and top coat), which is easy to apply, fast, time-saving and so on. Without the base and top coat as in the three step gel, the one step nail gel can be applied directly on the nail to achieve similar effects of gloss and durability in only two coats. Three step gel takes four procedures: 1 layer of base coat, 2 layers of color coat, and 1 layer of top coat. It is usually done in a manicure shop as it needs multiple procedures, complicated process and longer cure time. In comparison, the one step gel saves time, and its easy application makes DIY possible at home for similar outcomes as the three step nail gel polish.

Currently, the remover of the one-step gel polish on the market often contains substances such as acetone, ethyl acetate, and butyl acetate. And it often takes 8-15 minutes for fully soaked gel to come off. The remover has a pungent odor, and the long time of soak-off causes damage to the nail surface, the skin around, or allergies in some cases. The main ingredients of the remover are acetone, ethyl acetate, and butyl acetate which can have a detrimental effect on human' skin, eyes, mucosa, etc.

SUMMARY OF THE INVENTION

To remedy the deficiency of the existing one-step nail gel polish such as the need for toxic remover and damaging buffering before application, the present application provides an alcohol-removable nail gel polish and method of making the same. The alcohol removable gel polish, similar in application and function as common one-step gel polish, can be removed with alcohol solution (e.g., about 75% alcohol) which does not contain acetone, ethyl acetate, butyl acetate or toxic solvent. Using alcohol-soaked cotton to wrap nails for 10-15 min, the process is environmentally friendly, safe, healthy and not detrimental to human body.

Based on the present application, an alcohol-removable nail gel polish comprises the following components in percent by weight:
 Isobornyl acrylate 10-15%
 Hydroxyethyl methacrylate 15-25%
 Trimethylolpropane triacrylate 5-15%
 (2,4,6-trimethylbenzoyl)diphenylphosphine oxide 5-15%
 Aliphatic urethane acrylate 20-30%
 Cellulose acetate butyrate 15-20%
 Pigment 1-15%

Preferably, the alcohol-removable nail gel polish comprises the following components in percent by weight:
 Isoborneyl acrylate 12%
 Hydroxyethyl methacrylate 18%
 Trimethylolpropane triacrylate 10%
 (2,4,6-trimethylbenzoyl)diphenylphosphine oxide 7%
 Aliphatic urethane acrylate 24%
 Cellulose acetate butyrate 18%
 Pigment 11%.

Preferably, the alcohol-removable nail gel polish is a one-step gel polish that integrates base coat, color lacquer, and top coat.

Preferably, the pigment is selected from the group consisting of CI115850, CI15985, CI17200, CI77492, CI77510, CI77742, CI77491, CI77499, CI77891, and combinations thereof.

The above method for preparing an alcohol-removable nail polish comprises the following steps:
(1) mixing isobornyl acrylate, hydroxyethyl methacrylate, trimethylolpropane triacrylate, (2,4,6-Trimethylbenzoyl) diphenyl phosphine oxide and stirring until they are fully blended;
(2) adding aliphatic urethane acrylate, cellulose acetate butyrate in turn, and stirring until they are fully blended;
(3) adding pigments and mixing until even, then obtaining alcohol-removable nail polish.

Preferably, the stirring speed in step (1) is 500-700 r/min, and the stirring time is 20-40 min.

Preferably, the stirring speed in step (2) is 700-900 r/min, and the stirring time is 90-120 min.

Preferably, the stirring speed in step (3) is 400-500 r/min, and the stirring time is 5-120 min.

Users may apply the above-mentioned alcohol-removable nail polish on nails, cure under the UV light for 120 seconds, or 60 seconds LED light, or 30-60 seconds under UV-LED dual light. The gel polish stays on for 15 days or so. Therefore, the alcohol-removable nail gel polish according to the present invention has advantages of short curing time, easy application, and long-lasting wear.

To remove this gel polish, a cotton soaked with 70-80% alcohol or a mixture of ethanol and propylene glycol, preferably 75% of medical alcohol, is wrapped around the nails for 10-15 minutes. Such a gel removal process is free of toxins, such as acetone, ethyl acetate, and butyl acetate, and is environmentally friendly, safe and healthy, causing no damages to nail bed.

Some of the advantages of the present invention are summarized below:
(1) The present invention uses UV resin as a raw material, and the resulting gel polish has low odor, excellent softness and flexibility, strong adhesiveness, and high gloss. It has excellent overall performance, and satisfies environmental protection criteria and healthy standards;
(2) The nail gel polish is three-in-one (combining base coat, color and top coat), easy to apply, time-saving and can be done easily by DIY at home;
(3) After application, the gel can be cured under UV or LED light between 30-120 seconds and can last for over two weeks; and
(4) The gel remover (70-80% alcohol or ethyl alcohol and propylene glycol) used for removing the polish does not contain toxic solvents such as acetone, is safe, environmentally friendly, and healthy, avoiding harms to both the nail technicians and customers.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PRESENTLY PREFERRED EMBODIMENTS

The following examples are provided to illustrate, but not to limit, the present invention.

Example 1

An alcohol-removable nail polish according to an embodiment of the present invention comprises the following components in percent by weight:
Isoborneyl acrylate 12%
Hydroxyethyl methacrylate 18%
Trimethylolpropane triacrylate 10%
(2,4,6-trimethylbenzoyl)diphenylphosphine oxide 7%
Aliphatic urethane acrylate 24%
Cellulose acetate butyrate 18%
CI15850 9%
CI77891 2%

The method for preparing the alcohol-removable nail gel comprises the following steps:
(1) mixing Isobornyl acrylate, hydroxyethyl methacrylate, trimethylolpropane triacrylate, (2,4,6-Trimethyl benzoyl) diphenyl phosphine oxide and stir at a speed of 600 r/min for 30 min until fully blended;
(2) adding aliphatic urethane acrylate and cellulose acetate butyrate in sequence and stir at a speed of 800 r/min for 105 minutes until fully blended; and
(3) adding CI15850 and CI77891 and stirring at a speed of 450 r/min for 15 min until fully blended to make the alcohol-removable nail gel polish.

Example 2

An alcohol-removable nail polish according to another embodiment of the present invention comprises the following components in percent by weight:
Isobornyl acrylate 15%
Hydroxyethyl methacrylate 17%
Trimethylolpropane triacrylate 5%
(2,4,6-trimethylbenzoyl)diphenylphosphine oxide 8.5%
Aliphatic urethane acrylate 30%
Cellulose acetate butyrate 18%
CI177499 6.5%

The method for preparing the alcohol-removable nail gel comprises the following steps:
mixing isobornyl acrylate, hydroxyethyl methacrylate, trimethylolpropane triacrylate, (2,4,6-Trimethyl benzoyl) diphenyl phosphine oxide and stir at a speed of 700 r/min for 20 min until fully blended;
adding aliphatic urethane acrylate, cellulose acetate butyrate, and stir at a speed of 900 r/min for 90 minutes until fully blended; and
adding CI77499 and stirring at a speed of 500 r/min for 5 min until fully blended to make the alcohol-removable nail gel polish.

Example 3

An alcohol-removable nail polish according to yet another embodiment of the present invention comprises the following components in percent by weight:
Isobornyl acrylate 10%
Hydroxyethyl methacrylate 20%
Trimethylolpropane triacrylate 15%
(2,4,6-trimethylbenzoyl)diphenylphosphine oxide 5%
Aliphatic urethane acrylate 20%
Cellulose acetate butyrate 20%
CI15985 3%
CI77510 2%
CI77891 4%
CI15850 1%.

The method for preparing the alcohol-removable nail glue includes the following steps:
(1) Mixing isobornyl acrylate, hydroxyethyl methacrylate, trimethylolpropane triacrylate, (2,4,6-Trimethylbenzoyl) diphenyl phosphine oxide and stirring at a speed of 500 r/min for 40 minutes until fully blended;
(2) Adding aliphatic urethane acrylate, cellulose acetate butyrate in succession and stirring at a speed of 700 r/min for 120 minutes until fully blended;
(3) Adding CI15985, CI77891, CI77510, CI15850 and stirring at a speed of 400 r/min for 25 minutes until fully blended; then this type of alcohol removable nail gel is made.

The alcohol-removable nail polish obtained in the examples of the present invention above were tested, and the results are illustrated as below in Table 1:

TABLE 1

Performance Test Results of Alcohol Removable Nail Gel

| Test Item | Tests | Results |
|---|---|---|
| High Temperature Test | Keep under temperature at 150° F. (70° C.) for 5 days, and then cool down room temperature. Observe whether the color changes, whether the cure is normal and whether there is caking. | Colors remain normal; Cured as desired and no caking. |
| Low Temperature Test | Keep temperature below 23° F. (−5° C.) for 24 hour and return to room temperature to observe whether the color changes, whether the cure is normal and whether there is caking. | Colors remain normal; Cured as desired and no caking. |
| Firmness Test | In room temperature (59° F.-77° F.), scrub clean a piece of glass with alcohol. After the glass is dry, apply one layer of the gel after cured for 120 seconds under UV light, and cut a grid of five lines to observe whether there is falling off. | No fall off observed. |
| Hygiene Test | Total amount of bacteria ≤1000 CFU/g Total amount of mold and yeast ≤100 CFU/g | Total amount of bacteria <10 CFU/g Total amount of mold and yeast <10 CFU/g |
| Nail Test | To observe whether there is chipping in 10 days in normal wear | No chipping observed for 10 days |

Table 1 shows that alcohol-removable nail gels according to this invention perform well in high and low temperature, and have exceeded the requirement of firmness and hygiene, and hence satisfies consumers' demand.

Contrast Test 1: Comparison of the removal process with other types of one step nail gel

TABLE 2

| | Comparison of different nail gels | |
| --- | --- | --- |
| | Oily nail | Dry nail |
| This Invention | Wrapped with 75% alcohol after 8-10 minutes and gently file off. | Wrapped with 75% alcohol after 8-10 minutes and gently file off. |
| Other types of one step gel | Wrapped with acetone after 8-10 minutes and gently file off. | Covered with acetone after 8-10 minutes and gently file off. |

Table 2 shows that other types of one step gel requires 8 to 10 minutes soak-off time with acetone solvents or alike, and this invention needs about 8-15 minutes to remove with 75% alcohol, which is more environmentally friendly, and healthy.

We claim:

1. An alcohol-removable nail gel comprising the following components in percent by weight:
   isobornyl acrylate 10-15%
   hydroxyethyl methacrylate 15-25%
   trimethylolpropane triacrylate 5-15%
   (2,4,6-trimethylbenzoyl)diphenylphosphine oxide 5-15%
   aliphatic urethane acrylate 20-30%
   cellulose acetate butyrate 15-20%
   pigment 1-15%.

2. The alcohol-removable nail gel of claim 1 comprising the following in percent by weight:
   isoborneyl acrylate 12%
   hydroxyethyl methacrylate 18%
   trimethylolpropane triacrylate 10%
   (2,4,6-trimethylbenzoyl)diphenylphosphine oxide 7%
   aliphatic urethane acrylate 24%
   cellulose acetate butyrate 18%
   pigment 11%.

3. The alcohol-removable nail gel of claim 1 being a three-in-one nail gel, in which base coat, color lacquer, and top coat are combined for a one-step application.

4. The alcohol-removable nail gel of claim 1 wherein the pigment is selected from the group consisting of CI15850, CI15985, CI17200, CI77492, CI77510, CI77742, CI77491, CI77499, CI77891, and combinations thereof.

5. A method of making the alcohol-removable nail gel of claim 1 comprising the following steps:
   (1) mixing isobornyl acrylate, hydroxyethyl methacrylate, trimethylolpropane triacrylate, (2,4,6-trimethyl) benzoyl) diphenylphosphine oxide to form a first mixture, and stirring the first mixture;
   (2) adding aliphatic urethane acrylate and cellulose acetate butyrate into the first mixture of step (1) to form a second mixture and stirring the second mixture;
   (3) adding the pigment to form a third mixture and stirring the third mixture to make the alcohol removable gel.

6. The method of claim 5 wherein in step (1), the stirring step is carried at a speed of 500-700 r/min for 20-40 minutes.

7. The method of claim 5 wherein in step (2), the stirring is carried out at a speed of 700-900 r/min for 90-120 minutes.

8. The method of claim 5 wherein in step (3), the stirring is carried out at a speed of 400-500 r/min for 5-120 minutes.

* * * * *